United States Patent [19]
Gozzo et al.

[11] 3,975,180
[45] Aug. 17, 1976

[54] CRYSTALLINE ADDUCTS OF CARBAMOYL SULPHOXIDES AND UREA IN A 1:3 RATIO

[75] Inventors: Franco Gozzo, S. Donato Milanese (Milan); Marcella Masoero, Milan; Ernesto Signorini, Malnate (Varese); Riccardo Fabbrini, Milan, all of Italy

[73] Assignee: Montedison S.p.A., Milan, Italy

[22] Filed: June 6, 1975

[21] Appl. No.: 584,352

[30] Foreign Application Priority Data
June 7, 1974 Italy .................................. 23725/74

[52] U.S. Cl. .................................. 71/103; 71/88; 71/90; 71/91; 71/94; 71/95; 260/239 BF; 260/243 B; 260/247.1 R; 260/293.85; 260/326.82; 260/551 R; 260/553 R

[51] Int. Cl.² .................. A01N 9/14; C07C 125/00; C07C 127/00

[58] Field of Search .................. 71/99, 103, 98; 260/553 R, 551 R

[56] References Cited
UNITED STATES PATENTS

| | | | |
|---|---|---|---|
| 3,594,362 | 7/1971 | Szabo | 71/99 X |
| 3,816,435 | 6/1974 | Walker | 71/94 X |
| 3,816,436 | 6/1974 | Walker | 71/94 X |
| 3,879,455 | 4/1975 | Tilles | 71/103 X |
| 3,896,169 | 7/1975 | Tilles | 260/551 R |
| 3,910,935 | 10/1975 | Walker | 71/94 X |

*Primary Examiner*—Joseph Paul Brust
*Attorney, Agent, or Firm*—Stevens, Davis, Miller & Mosher

[57] ABSTRACT

Novel crystalline adducts of a carbamoyl sulphoxide and urea have the formula

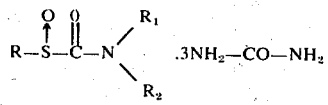

wherein R is substituted or unsubstituted aryl, alkyl or alkenyl; $R_1$ and $R_2$, which may be the same or different, are H, substituted or unsubstituted alkyls, alkenyls or aryls, or aliphatic groups that, bound to one another in the form of a chain $-(CH_2)_p-(X)_n-(CH_2)_q-$ (in which $p = 1,2,3$; $q = 1,2,3$; $X$, $=O$, $=S$, $=SO$, $=SO_2$; $n = 0$ or $1$), form with N a ring when $n = 1$ and $(p+q) \leq 4$. The adducts have herbicidal properties and herbicide compositions containing the adducts as well as process for inhibiting the growth of plants or for destroying them are contemplated.

14 Claims, No Drawings

CRYSTALLINE ADDUCTS OF CARBAMOYL SULPHOXIDES AND UREA IN A 1:3 RATIO

This invention relates to adducts of carbamoyl sulphoxides and urea which are stable, crystalline adducts having interesting, long-lasting herbicidal properties. More particularly, this invention relates to the said adducts, the method of preparing same and compositions containing them.

A prior patent application filed on Oct. 5, 1973, U.S. Ser. No. 403,820 assigned to the assignee of this application describes carbamoyl sulphoxides having the general formula:

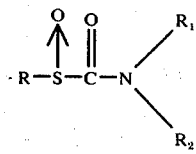

wherein R is an aryl, alkyl or alkenyl which may be unsubstituted or substituted; $R_1$ and $R_2$, the same or different, are H, alkyls, alkenyls or aryls, which may be unsubstituted or substituted, or aliphatic groups that, bound to one another in the form of a chain $-(CH_2)_p - (X)_n - (CH_2)_q -$ (in which $p = 1,2,3$; $q = 1,2,3$; $X = >O; >S; >SO$ or $>SO_2$ and $n = 0$ or 1), form with N - when $n = 1$ and $(p+q) \leq 4$ - a ring. Such carbamoyl sulphoxides exert an interesting herbicidal action towards both monocotyledons and infesting latifoliae, while they are innocuous towards important agrarian cultures.

It is an object of the present invention to provide a new class of crystalline adducts of carbamoyl sulphoxides and urea which have good thermal stability and retain at least the herbicidal activity typical of the carbamoyl sulphoxides.

Another object of this invention is to provide herbicide adducts capable of gradually and regularly releasing the active substance, once they are applied to the soil.

A further object of the invention is to provide herbicides which are easy to formulate.

A still further object is to provide a method of preparing the adducts provided by the invention.

These and still other objects are achieved by providing adducts of carbamoyl sulphoxides and urea having the general formula:

$$R-S(=O)-C(=O)-N(R_1)(R_2) \cdot 3\ NH_2-C(=O)-NH_2 \quad (I)$$

wherein R is a substituted or unsubstituted aryl, alkyl or alkenyl radical; $R_1$ and $R_2$ may be the same or different and are H, alkyls, alkenyls or aryls which may or may not be substituted, or aliphatic groups that, bound to one another in the form of a chain $-(CH_2)_p-(X)_n-(CH_2)_q-$ (in which $p = 1,2,3$; $q = 1,2,3$; X is $=O$; $=S$; $=SO$ or $=SO_2$ and $n = 0$ or 1), form with N — when $n = 1$ and $(p+q) \leq 4$ — a ring. Such adducts are solid and crystalline. They exhibit, on infrared spectrophotometric analysis, a shifting of the frequencies relevant to the vibrations of bonds N-H, N-C-N and S-O with respect to the corresponding ones of the urea and of the starting carbamoyl sulphoxides. On X-ray analysis, they exhibit spectral lines different from those typical of urea and of the starting carbamoyl sulphoxides if the latter are in the solid state and their centesimal composition is in accordance with formula (I).

The following Table 1 lists examples of some adducts falling under the general formula of the present invention, near which the infrared frequencies characteristic of the most meaningful bonds are indicated by way of comparison with the frequencies relating to urea. The shifting of the main band due to bond $S \rightarrow O$ is reported as the difference - in $cm^{-1}$ — between the frequency of the most intense band due to such grouping in the adduct and the frequency of the main band of group $S \rightarrow O$ in the starting carbamoyl sulphoxide ($\Delta \gamma$).

TABLE 1

Infrared frequency of adducts having general formula I as compared with those of the components.

| ADDUCT | | | FREQUENCY OF BONDS ($cm^{-1}$) | | $\Delta\gamma(cm^{-1})$ of group $S \rightarrow O$ with respect to each carbamoyl sulphoxide |
|---|---|---|---|---|---|
| Item No. | R | $R_1 = R_2$ | N—C—N | N—H | |
| 5675 U | $CH_3$ | iso $C_4H_9$ | 799 | 3378 – 3185 | – 8 |
| 5105 U | $C_2H_5$ | n. $C_3H_7$ | 797 | 3367 – 3185 | – 5 |
| 5286 U | $C_2H_5$ | iso $C_4H_9$ | 797 | 3390 – 3195 | – 2 |
| 5197 U | n. $C_3H_7$ | n. $C_3H_7$ | 799 | 3378 – 3185 | – 6 |
| 5451 U | n. $C_3H_7$ | i. $C_4H_9$ | 796 | 3390 – 3185 | – 16 |
| 5193 U | iso $C_3H_7$ | n. $C_3H_7$ | 800 | 3370 – 3185 | – 22 |
| 5452 U | iso $C_3H_7$ | iso $C_4H_9$ | 795 | 3390 – 3185 | $\{ -4, -2 \}$ |
| 5517 U | iso $C_4H_9$ | iso $C_4H_9$ | 795 | 3390 – 3185 | – 9 |
| 5104 U | $C_6H_5CH_2$ | n. $C_3H_7$ | 797 | 3356 – 3185 | – 3 |
| UREA | | | 787 | 3450 – 3355 | — |

The adducts of this invention, unlike the most interesting terms of the carbamoyl sulphoxides series, are stable in storage and can be indefinitely preserved at room temperature.

For purposes of comparison with the thermal stability of the carbamoyl sulphoxides as such, Table 2 reports the percentages of carbamoyl sulphoxide recovered from the corresponding adduct after residence at temperatures higher than room temperature, along with the percentages of same recovered after conditioning of carbamoyl sulphoxide as such at 50°C. and 100°C.

The recovery of carbamoyl sulphoxide from the adduct at the conclusion of the conditioning period is carried out by extraction with chloroform: the dose of carbamoyl sulphoxide in the extracts is determined by chromatography on a thin layer or by gas-chromatograhy according to conventional techniques.

TABLE II

Percentages of carbamoyl sulphoxide recovered from the adduct after 14 days at 54°C and after 8 hrs. at 100°C in comparison with the carbamoyl sulphoxide present after treatment at 50°C for 13 days and at 100°C for 8 hrs.

| | Adduct | | % Of Carbamoyl Sulphoxide Recovered | | | |
| | | | From Carbamoyl Sulphoxide | | From The Adduct | |
| Item No. | R | $R_1 = R_2$ | 50°C; 13 days | 100°C; 8 hrs | 54°C; 14 days | 100°C; 8 hrs |
|---|---|---|---|---|---|---|
| 5105 U | $C_2H_5$ | n. $C_3H_7$ | 87 | ~ 51 | 90 | 75 |
| 5197 U | n. $C_3H_7$ | n. $C_3H_7$ | 74 | ~ 0 | 87 | 63 |
| 5451 U | n. $C_3H_7$ | iso $C_4H_9$ | 75 | ~ 0 | 95 | 80 |
| 5193 U | iso $C_3H_7$ | n. $C_3H_7$ | 24 | ~ 0 | 96 | 91 |
| 5452 U | iso $C_3H_7$ | iso $C_4H_9$ | 50 | ~ 0 | 96 | 89 |

The adducts corresponding to formula I may be obtained through a very simple process, which is also an object of this invention and consists in adding the carbamoyl sulphoxide to a solution of urea in a suitable solvent, and in concentrating such mixture. The adduct precipitates and is then collected and dried.

When the carbamoyl sulphoxide : urea molar ratios are = 1:3, the solvent may be also evaporated to dryness.

The formation and composition of the adduct corresponding to formula I are proved by the fact that, even if the carbamoyl sulphoxide is mixed with a urea solution in molar ratios other than 1:3, the precipitate obtained by concentration always consists in a white crystalline solid, wherein the molar ratios are those indicated by formula I and wherein the frequencies of the bands characteristic of the spectrum and the spectral lines of the Debye-diagram are different from those of the starting compounds.

Since the adduct can be easily crystallized and the carbamoyl sulphoxide is easily recoverable from same by mild hydrolysis and/or extraction with chloroform or another proper solvent, it is evident that the adduct formation may be utilized to purify the carbamoyl sulphoxide.

The herbicidal activity of the adducts provided by this invention is no lower than the activity of the corresponding carbamoyl sulphoxide as such when the doses applied to the soil, calculated as carbamoyl sulphoxide content, are equal.

The following examples are given better to illustrate the present industrial invention.

EXAMPLE 1

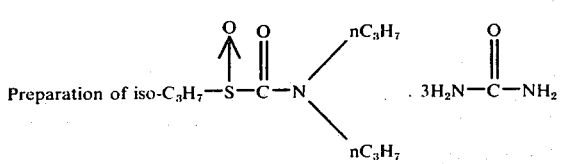

Preparation of iso-$C_3H_7$—S—C—N(nC$_3$H$_7$)(nC$_3$H$_7$) . 3H$_2$N—C—NH$_2$ (5193 - U) from carbamoyl sulphoxide and urea in a 1 : 3 molar ratio. 3 g of isopropyl-N-di-n-propylcarbamoyl sulphoxide were added to 13.84 g of a methanol solution containing 2.48 g of urea. By slow evaporation under vacuum at room temperature the following four precipitate fractions were successively isolated which, after drying, were weighed and subjected to elemental analysis, the results thus obtained being reported in the following Table III.

TABLE III

| Fraction | Adduct Weight, g | Elemental Analysis | | | |
| | | C % | H % | N % | S % |
|---|---|---|---|---|---|
| I | 1.905 | 38.56 | 8.30 | 24.78 | 8.06 |
| II | 1.658 | 38.63 | 8.23 | 24.75 | 7.94 |
| III | 0.260 | 39.05 | 8.31 | 24.82 | 7.76 |
| IV | 0.770 | 38.05 | 8.16 | 25.07 | 7.40 |
| Theoretical Analysis: | | 39.08 | 8.32 | 24.54 | 8.02 |

All of the four fractions thus obtained, when subjected to X-ray analysis, produced Debye-diagrams containing the same spectral lines, sharply differentiated from those typical of urea.

The infrared spectra of the fractions were also like one another and contained the absorption bands shown in Table I.

EXAMPLE 2

Preparation of 5193 - U starting from carbamoyl sulphoxide and urea in molar ratios different from 1 : 3. 0.505 g of isopropyl-N-di-n-propylcarbamoyl sulphoxide was added to 0.760 g of a methanol solution containing 0.136 g of urea (initial molar ratio of the reagents in the order indicated : 1:0.98). After having allowed the solution to stand, a precipitate was collected that, after drying, weighed 0.202 g, and from whose elemental analysis the following results were obtained:

| C% | H% | N% | S% |
|---|---|---|---|
| 39.52 | 8.54 | 24.63 | 7.47 |

The infrared spectrum and the Debye-diagram of this precipitate are like the corresponding spectra relative to the precipitates obtained in Example 1.

Thoroughly similar results were obtained starting from the following starting amounts of reagents:

0.268 g of isopropyl-N-di-n-propylcarbamoyl sulphoxide;

1.921 g of a methanol solution containing 0.344 g of urea (initial molar ratio between the two reagents = 1 : 4.68).

EXAMPLE 3

By operating according to the method described in Example 1, the compounds reported on Table I were prepared, whose adduct nature is proved by the most meaningful I.R. frequencies reported on aforesaid table. Individual samples of these adducts resulted in a correct elemental analysis.

Similar results were obtained by employing, during preparation, a urea-saturated aqueous solution.

EXAMPLE 4

Herbicide activity tests.

Adduct M 5193 - U, prepared according to the method of Example 1, by collecting all the fractions until thorough evaporation of the solvent, was divided into two equal samples.

One of these samples was further treated according to known formulation techniques, thus obtaining a cellulose powder containing the 2% of adduct (Sample 2).

On both the adduct (Sample 1) and the solid formulate (Sample 2), herbicidal activity tests were carried out in comparison with the corresponding carbamoyl sulphoxide as such.

Sample 1 was dissolved in a hydroacetone solution at 25% by volume of acetone. This solution was sprayed onto the earth contained in boxes measuring 40 × 30 × 20 cm, in whose upper part, a 5 cm thick layer, the seeds of the following infesting weeds had been uniformly distributed:

The 5 cm layer wherein these seeds were distributed had been laid onto a previously humidified soil. Under thoroughly identical conditions, as many boxes were prepared by spraying sample 2 (prepared in powder at the indicated titra, on a cellulose support) onto the surface and, for comparative purposes, a third set of as many likewise prepared boxes, onto which a hydroacetone solution of the carbamoyl sulphoxide as such was sprayed.

The process was repeated on further three sets of boxes, into which the preparations were incorporated by hoeing the first 5 cm of the upper layer.

The doses of each preparation were selected so as to apply to the soil amounts equal to 0.250; 0.500; 1 and 2 kg/ha respectively, calculated as carbamoyl sulphoxide.

After a 28-day residence in a glasshouse (temperature: 15° to 22°C. and regular daily irrigations), the results obtained are those reported in the following Table IV, using the activity indexes indicated hereinbelow:

| 0 | = | no activity |
| 1; 2 | = | insufficient activity |
| 3 | = | high activity |
| 4 | = | total activity |

TABLE IV

Herbicide activity in a glasshouse of adduct 5193 U according to the invention as compared with that of the corresponding carbamoyl sulphoxide

| Applied product | Dose Kg/ha of carbamoyl sulphoxide | Application by incorporation | | | | | | | | | |
|---|---|---|---|---|---|---|---|---|---|---|---|
| | | MONOCOT. | | | | | | DICOT. | | | |
| | | ECHINO-CHLOA | AVENA FATUA | LOL-IUM | SOR-GHUM | SET-ARIA | STEL-LARIA | IPO-MEA | VIG-NA | RU-MEX | GALIN-SOGA |
| Hydroacetone solution of adduct 5193 - Urea | 0.25 | 3 | 3 | 4 | 4 | 4 | 3 | 1 | 2 | 0 | 0 |
| | 0.50 | 4 | 3 | 4 | 4 | 4 | 4 | 2 | 3 | 1 | 1 |
| | 1.00 | 4 | 4 | 4 | 4 | 4 | 4 | 3 | 4 | 3 | 3 |
| | 2.00 | 4 | 4 | 4 | 4 | 4 | 4 | 4 | 4 | 4 | 4 |
| Powder containing 2% of adduct - Urea on cellulose support. | 0.25 | 3 | 3 | 4 | 4 | 4 | 2 | 0 | 2 | 0 | 0 |
| | 0.50 | 4 | 3 | 4 | 4 | 4 | 4 | 1 | 3 | 1 | 1 |
| | 1.00 | 4 | 4 | 4 | 4 | 4 | 4 | 3 | 4 | 3 | 3 |
| | 2.00 | 4 | 4 | 4 | 4 | 4 | 4 | 4 | 4 | 4 | 4 |
| Carbamoyl sulphoxide 5193 as such. | 0.25 | 3 | 1 | 4 | 4 | 4 | 2 | 0 | 1 | 0 | 0 |
| | 0.50 | 4 | 3 | 4 | 4 | 4 | 3 | 1 | 3 | 0 | 0 |
| | 1.00 | 4 | 4 | 4 | 4 | 4 | 4 | 2 | 3 | 1 | 1 |
| | 2.00 | 4 | 4 | 4 | 4 | 4 | 4 | 4 | 4 | 4 | 4 |

| Applied product | Dose Kg/ha of carbamoyl sulphoxide | Surface application | | | | | | | | | |
|---|---|---|---|---|---|---|---|---|---|---|---|
| | | MONOCOT. | | | | | | DICOT. | | | |
| | | ECHINO-CHLOA | AVENA FATUA | LOL-IUM | SOR-GUM | SET-ARIA | STEL-LARIA | IPO-MEA | VIG-NA | RU-MEX | GALIN-SOGA |
| Hydroacetone solution of adduct 5193 - Urea | 0.25 | 3 | 2 | 3 | 3 | 3 | 3 | 0 | 2 | 0 | 0 |
| | 0.50 | 4 | 3 | 4 | 4 | 4 | 3 | 1 | 3 | 1 | 1 |
| | 1.00 | 4 | 4 | 4 | 4 | 4 | 4 | 3 | 4 | 3 | 3 |
| | 2.00 | 4 | 4 | 4 | 4 | 4 | 4 | 4 | 4 | 4 | 4 |
| Powder containing 2% of adduct - Urea on cellulose support. | 0.25 | 3 | 2 | 3 | 2 | 2 | 2 | 0 | 2 | 0 | 0 |
| | 0.50 | 4 | 3 | 4 | 4 | 4 | 3 | 1 | 2 | 0 | 1 |
| | 1.00 | 4 | 4 | 4 | 4 | 4 | 4 | 3 | 4 | 2 | 2 |
| | 2.00 | 4 | 4 | 4 | 4 | 4 | 4 | 3 | 4 | 4 | 4 |
| Carbamoyl sulphoxide 5193 as such. | 0.25 | 3 | 0 | 1 | 0 | 1 | 3 | 2 | 2 | 0 | 0 |
| | 0.50 | 4 | 2 | 2 | 1 | 2 | 4 | 4 | 4 | 0 | 0 |
| | 1.00 | 4 | 2 | 4 | 4 | 4 | 4 | 2 | 3 | 1 | 2 |
| | 2.00 | 4 | 4 | 4 | 4 | 4 | 4 | 3 | 4 | 2 | 2 | monocotyledons: Echinochloa crus galli
Avena fatua
Lolium sp.
Sorghum sp.
Setaria glauca dicotyledons: Stellaria media
Ipomea sp.
Vigna Sinensis
Rumex Crispus
Galinsoga sp.

Although the invention has been described in detail for the purpose of illustration, it is to be understood that such detail is solely for that purpose and that variations can be made therein by those skilled in the art without departing from the spirit and scope of the invention except as it may be limited by the claims.

What we claim is:

1. A stable, crystalline adduct having the formula

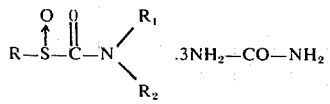

in which:
R is benzyl or an alkyl having from 1 to 4 carbon atoms, and
R₁ and R₂ may be the same or different and are alkyls having from 3 to 4 carbon atoms.

2. The adduct of formula:

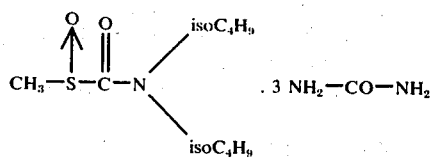

3. The adduct of formula:

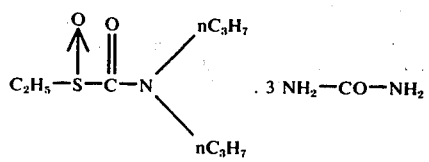

4. The adduct of formula:

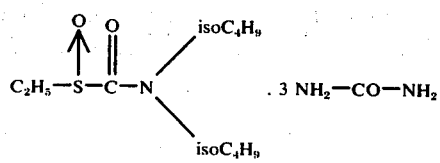

5. The adduct of formula:

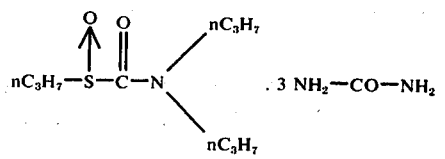

6. The adduct of formula:

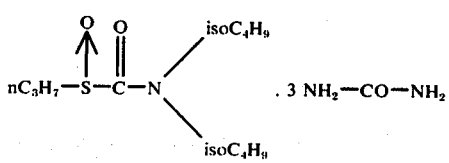

7. The adduct of formula:

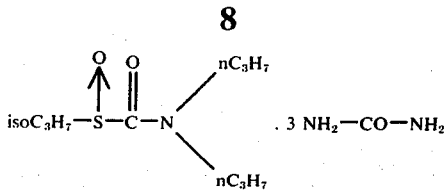

8. The adduct of formula:

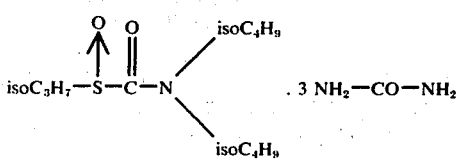

9. The adduct of formula:

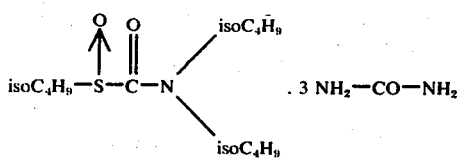

10. The adduct of formula

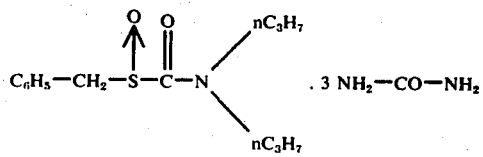

11. A process for preparing the adducts of claim 1, which comprises mixing a carbamoyl sulphoxide having the general formula

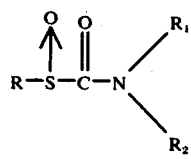

with a solution of urea in a solvent therefor, and recovering the resulting crystallized product; R, R₁ and R₂ being as defined in claim 1.

12. The process of claim 11 wherein the molar ratio of carbamoyl sulphoxide to urea is 1 : 3.

13. The process of claim 12 wherein the solvent is evaporated to dryness.

14. A process for inhibiting noxious plant growth which comprises scattering on or incorporating into the soil containing same at least 0.25 kg/ha of an adduct of claim 1.

* * * * *